United States Patent
Kawai et al.

(10) Patent No.: US 11,043,699 B2
(45) Date of Patent: Jun. 22, 2021

(54) NONAQUEOUS ELECTROLYTE SOLUTION AND METHOD FOR PRODUCING NONAQUEOUS ELECTROLYTE SECONDARY BATTERY

(71) Applicants: Toshiyuki Kawai, Nagoya (JP); Hiroto Asano, Nisshin (JP); Shigeaki Yamazaki, Osaka (JP); Shinichi Kinoshita, Osaka (JP)

(72) Inventors: Toshiyuki Kawai, Nagoya (JP); Hiroto Asano, Nisshin (JP); Shigeaki Yamazaki, Osaka (JP); Shinichi Kinoshita, Osaka (JP)

(73) Assignees: Toyota Jidosha Kabushiki Kaisha, Toyota (JP); Daikin Industries, Ltd., Osaka (JP)

( * ) Notice: Subject to any disclaimer, the term of this patent is extended or adjusted under 35 U.S.C. 154(b) by 201 days.

(21) Appl. No.: 15/883,611

(22) Filed: Jan. 30, 2018

(65) Prior Publication Data

US 2018/0219259 A1    Aug. 2, 2018

(30) Foreign Application Priority Data

Feb. 1, 2017    (JP) .............................. JP2017-017115

(51) Int. Cl.
*H01M 10/0568* (2010.01)
*C07D 317/36* (2006.01)
(Continued)

(52) U.S. Cl.
CPC ...... *H01M 10/0568* (2013.01); *C07D 317/36* (2013.01); *C07F 5/025* (2013.01);
(Continued)

(58) Field of Classification Search
CPC .. C07D 317/36; C07F 5/025; H01M 10/0525; H01M 2300/0025; H01M 10/0568;
(Continued)

(56) References Cited

U.S. PATENT DOCUMENTS

2006/0216612 A1    9/2006   Jambunathan et al.
2011/0111305 A1*   5/2011   Jeon .................. H01M 10/0567
                                                        429/326

(Continued)

FOREIGN PATENT DOCUMENTS

CN    101635379 A    1/2010
CN    102496739 A    6/2012
(Continued)

*Primary Examiner* — Jonathan G Jelsma
*Assistant Examiner* — Omar M Kekia
(74) *Attorney, Agent, or Firm* — Dinsmore & Shohl LLP

(57) ABSTRACT

The present disclosure provides a nonaqueous electrolyte solution that is used in a nonaqueous electrolyte secondary battery. The nonaqueous electrolyte solution contains a fluorinated solvent, a predetermined additive A and a predetermined additive B. A ratio ($C_A/C_B$) of concentration $C_A$ (mol/L) of the additive A and concentration $C_B$ (mol/L) of the additive B lies in a range of 1 to 30.

20 Claims, 1 Drawing Sheet

(51) Int. Cl.
*C07F 5/02* (2006.01)
*H01M 10/0567* (2010.01)
*H01M 10/0525* (2010.01)
*H01M 10/0569* (2010.01)

(52) U.S. Cl.
CPC .... *H01M 10/0567* (2013.01); *H01M 10/0525* (2013.01); *H01M 10/0569* (2013.01); *H01M 2300/0025* (2013.01); *H01M 2300/0034* (2013.01)

(58) Field of Classification Search
CPC ..... H01M 10/0569; H01M 2300/0034; H01M 10/0567
USPC ......................................................... 429/332
See application file for complete search history.

(56) References Cited

U.S. PATENT DOCUMENTS

| | | | |
|---|---|---|---|
| 2015/0270578 A1 | 9/2015 | Nakatsutsumi et al. | |
| 2016/0233544 A1* | 8/2016 | Kim | H01M 10/0567 |
| 2017/0133716 A1* | 5/2017 | Masuda | H01M 2/14 |
| 2018/0183101 A1* | 6/2018 | Mizutani | H01M 10/0567 |

FOREIGN PATENT DOCUMENTS

| | | |
|---|---|---|
| CN | 104934638 A | 9/2015 |
| JP | 2006202745 A | 8/2006 |
| JP | 2007165125 A | 6/2007 |
| JP | 2008235008 A | 10/2008 |
| JP | 2012043627 A | 3/2012 |
| JP | 2012190771 A | 10/2012 |
| WO | 2014108979 A1 | 7/2014 |

* cited by examiner

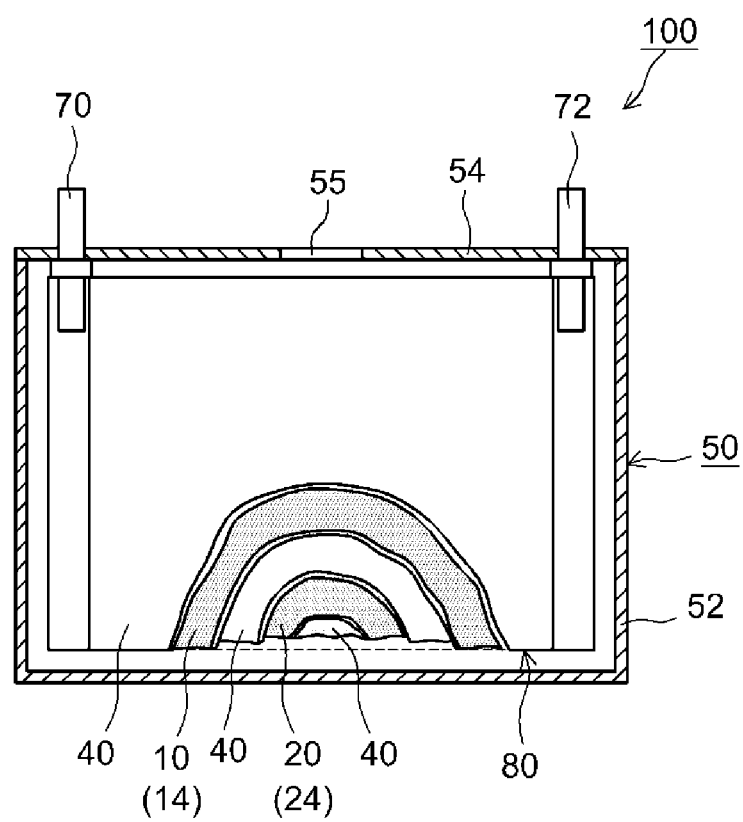

NONAQUEOUS ELECTROLYTE SOLUTION AND METHOD FOR PRODUCING NONAQUEOUS ELECTROLYTE SECONDARY BATTERY

CROSS-REFERENCE TO RELATED APPLICATIONS

The present application claims priority to Japanese Patent Application No. 2017-17115 filed on Feb. 1, 2017, the entire contents of which are incorporated in the present specification by reference.

BACKGROUND

1. Technical Field

The present disclosure relates to a nonaqueous electrolyte solution and to a method for producing a nonaqueous electrolyte secondary battery.

2. Description of the Related Art

Nonaqueous electrolyte secondary batteries such as lithium ion secondary batteries are smaller, lighter and afford higher energy densities than other existing batteries. Nonaqueous electrolyte secondary batteries have accordingly come to be used, in recent years, as power sources for vehicle driving in hybrid cars, electric cars and the like. Part of the nonaqueous electrolyte solution in such nonaqueous electrolyte secondary batteries decomposes generally during initial charging, and a protective coating film (solid electrolyte interface film: SEI film) containing decomposition products of the foregoing is formed on the surface of the negative electrode. The interface between the negative electrode and the nonaqueous electrolyte solution is stabilized by such a SEI film, and thus the durability (for instance cycle characteristics) of the battery can be enhanced. Examples of related prior art documents include for instance Japanese Patent Application Publication No. 2007-165125. For instance, Japanese Patent Application Publication No. 2007-165125 discloses a feature wherein the durability of a battery can be enhanced by incorporating lithium difluorooxalatoborate (LiDFOB) in a nonaqueous electrolyte solution, to thereby form a SEI film containing components derived from LiDFOB, on the surface of the negative electrode.

SUMMARY

Electrolyte solutions obtained by dissolving a supporting salt (for instance a lithium salt) in a carbonate-based solvent such as ethylene carbonate, propylene carbonate, diethyl carbonate or the like are used as electrolyte solutions that are utilized in nonaqueous electrolyte secondary batteries. In terms of further enhancing the performance of the secondary battery (for instance increasing energy density), however, electrolyte solutions in which there are used solvents less prone to oxidizing than such carbonate-based solvents can be used. Fluorinated solvents (solvents having fluorine atoms introduced in the molecule) have been studied as solvents that oxidize less readily than carbonate-based solvents. However, it has been occasionally observed that when an additive such as LiDFOB described above is also used in cases where a fluorinated solvent is utilized as an electrolyte solution solvent, a good coating film cannot be formed on the negative electrode, and cycle durability (for instance capacity retention rate after cycling) is insufficient.

It is an object of the present disclosure, arrived at in the light of the above considerations, to provide a nonaqueous electrolyte solution excellent in oxidation resistance and that allows realizing high durability. A further object of the disclosure is to provide a method for producing a nonaqueous electrolyte secondary battery that is equipped with such a nonaqueous electrolyte solution.

In the present specification there is provided a nonaqueous electrolyte solution used in a nonaqueous electrolyte secondary battery. The nonaqueous electrolyte solution contains a fluorinated solvent, an additive A represented by General Formula (I) and an additive B represented by General Formula (II). A ratio ($C_A/C_B$) of the concentration $C_A$ (mol/L) of the additive A and the concentration $C_B$ (mol/L) of the additive B in the nonaqueous electrolyte solution lies in the range of 1 to 30.

[C1]

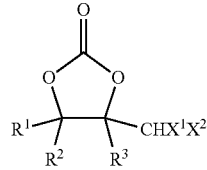

(I)

Wherein, $R^1$ to $R^3$ (i.e., $R^1$, $R^2$, and $R^3$) are selected, each independently, from the group consisting of hydrogen atoms, fluorine atoms, methyl groups, fluoromethyl groups and difluoromethyl groups, and $X^1$ and $X^2$ are selected, each independently, from the group consisting of hydrogen atoms and fluorine atoms, where at least one from among $R^1$ to $R^3$, and $X^1$ and $X^2$, is a fluorine atom or a group containing a fluorine atom.

[C2]

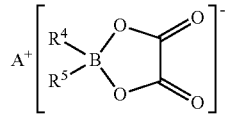

(II)

Wherein, $R^4$ and $R^5$ in the formula are selected, each independently, from among halogen atoms and perfluoroalkyl groups, and $A^+$ is a cation.

The cycle durability (for instance capacity retention rate after cycling) of the nonaqueous electrolyte secondary battery can be increased by combining the additive A represented by General Formula (I) and the additive B represented by General Formula (II) at a specific concentration ratio.

In some aspects of the nonaqueous electrolyte solution disclosed herein the solution contains, as the additive A, at least one carbonate selected from the group consisting of fluoropropylene carbonate and difluoropropylene carbonate. The effect of enhancing cycle durability is brought out more readily by an additive A having such a structure.

In some aspects of the nonaqueous electrolyte solution disclosed herein the solution contains lithium difluoroxalatoborate, as the additive B. The effect of enhancing cycle durability is brought out more readily by an additive B having such a structure.

The present disclosure provides also a method for producing a nonaqueous electrolyte secondary battery. The production method includes a step of constructing a battery assembly by accommodating a positive electrode and a negative electrode inside a battery case, together with a nonaqueous electrolyte solution, and an initial charging step of subjecting the battery assembly to an initial charging treatment. The nonaqueous electrolyte solution accommodated in the battery assembly contains a fluorinated solvent, the additive A represented by General Formula (I) and the additive B represented by General Formula (II), such that a ratio ($C_A/C_B$) of the concentration $C_A$ (mol/L) of the additive A and the concentration $C_B$ (mol/L) of the additive B in the nonaqueous electrolyte solution lies in the range of 1 to 30. The above production method allows producing a high-performance secondary battery excellent in cycle durability.

In some aspects, the nonaqueous electrolyte solution contains, as the additive A, at least one carbonate selected from the group consisting of fluoropropylene carbonate and difluoropropylene carbonate. In other aspects, the nonaqueous electrolyte solution contains lithium difluorooxalatoborate, as the additive B.

BRIEF DESCRIPTION OF THE DRAWINGS

FIG. 1 is a diagram illustrating schematically a lithium ion secondary battery according to an embodiment.

DETAILED DESCRIPTION

Embodiments of the present disclosure will be explained below with reference to accompanying drawings. The dimensional relationships in the figures (length, width, thickness and so forth) do not reflect actual dimensional relationships. Any features other than the matter specifically set forth in the present specification and that may be necessary for carrying out the present disclosure (for instance, the configuration and production method of an electrode body provided with a positive electrode and a negative electrode, the configuration and production method of a separator, the shape and so forth of a battery (case), as well as ordinary techniques pertaining to battery construction) can be regarded as instances of design matter for a person skilled in the art based on known techniques in the relevant technical field. The present subject matter can be realized on the basis of the disclosure of the present specification and common technical knowledge in the relevant technical field.

In the present specification the term "nonaqueous electrolyte secondary battery" refers to a secondary battery that is provided with a nonaqueous electrolytic solution (i.e., an electrolyte solution containing a supporting salt (supporting electrolyte) in a nonaqueous solvent). The term "lithium ion secondary battery" refers to a secondary battery that uses lithium ions as electrolyte ions and that is charged and discharged as a result of movement of lithium ions between the positive and negative electrodes. The term electrode active material denotes a material capable of reversibly storing and releasing a chemical species (lithium ions in a lithium ion secondary battery) that constitutes a charge carrier. A nonaqueous electrolyte solution that is used in lithium ion secondary batteries will be explained below, but the scope of use of the present disclosure is not meant to be limited thereto.

Nonaqueous Electrolyte Solution

A nonaqueous electrolyte solution according to some embodiments of the technology disclosed herein is a nonaqueous electrolyte solution used in lithium ion secondary batteries, the solution being liquid at normal temperature (for instance at 25° C.). In some embodiments, the solution may be a liquid at all times within a service temperature range (for instance −20° C. to 60° C.). Such a nonaqueous electrolyte solution contains a fluorinated solvent, a supporting salt, an additive A and an additive B.

Supporting Salt

Various materials known to be usable as supporting salts (lithium salts) in nonaqueous electrolyte solutions of lithium ion secondary batteries can be used herein, without particular limitations, as the supporting salt. Examples of supporting salts include for instance $LiPF_6$, $LiBF_4$, $LiAsF_6$, $LiCF_3SO_3$, $LiC_4F_9SO_3$, $Li(CF_3SO_2)_2N$, $LiC(CF_3SO_2)_3$, $LiSiF_6$, $LiClO_4$ and the like. The foregoing can be used singly or in combinations of two or more types. The concentration of the supporting salt may be set to lie in the range of 0.5 mol/L to 3.0 mol/L, or from 0.5 mol/L to 2.0 mol/L.

Fluorinated Solvent

Various materials usable as nonaqueous solvents in nonaqueous electrolyte solutions of lithium ion secondary batteries, and being partially substituted with fluorine (F), can be used herein as the fluorinated solvent, without particular limitations. For instance fluorinated cyclic carbonates and fluorinated linear carbonate may be used as the fluorinated solvent. Examples of fluorinated cyclic carbonates include for instance monofluoroethylene carbonate (MFEC), difluoroethylene carbonate, 4,4-difluoroethylene carbonate, trifluoroethylene carbonate, trifluoropropylene carbonate (TFPC), perfluoroethylene carbonate and the like. Examples of fluorinated linear carbonates include for instance fluoromethylmethyl carbonate, difluoromethylmethyl carbonate, trifluoromethylmethyl carbonate, fluoromethyldifluoromethyl carbonate, bis(fluoromethyl) carbonate, bis(difluoromethyl) carbonate, bis(trifluoromethyl) carbonate, (2-fluoroethyl)methyl carbonate, ethylfluoromethyl carbonate, (2,2-difluoroethyl)methyl carbonate, (2-fluoroethyl)fluoromethyl carbonate, ethyldifluoromethyl carbonate, (2,2,2-trifluoroethyl)methyl carbonate, (2,2-difluoroethyl)fluoromethyl carbonate, (2-fluoroethyl)difluoromethyl carbonate, ethyltrifluoromethyl carbonate, ethyl-(2-fluoroethyl) carbonate, ethyl-(2,2-difluoroethyl) carbonate, bis(2-fluoroethyl) carbonate, ethyl-(2,2,2-trifluoroethyl) carbonate, 2,2-difluoroethyl-2'-fluoroethyl carbonate, bis(2,2-difluoroethyl) carbonate, 2,2,2-trifluoroethyl-2'-fluoroethyl carbonate, 2,2,2-trifluoroethyl-2',2'-difluoroethyl carbonate, bis(2,2,2-trifluoroethyl) carbonate, pentafluoroethylmethyl carbonate, pentafluoroethylfluoromethyl carbonate, pentafluoroethylethyl carbonate, bis(pentafluoroethyl) carbonate and the like.

A combined system of the above fluorinated cyclic carbonate and the above fluorinated linear carbonate may be used as the fluorinated solvent. For instance, the mixing ratio of the fluorinated cyclic carbonate and the fluorinated linear carbonate may lie in the range of 20:80 to 40:60 by volume.

The nonaqueous electrolyte solution disclosed herein may contain a nonaqueous solvent (hereafter also referred to as non-fluorinated solvent) other than the fluorinated solvent, so long as the effect of the present subject matter is not impaired thereby. Examples of such non-fluorinated solvents include for instance ethylene carbonate (EC), propylene carbonate (PC), diethyl carbonate (DEC), dimethyl carbonate (DMC), ethyl methyl carbonate (EMC), 1,2-dimethoxyethane, 1,2-diethoxyethane, tetrahydrofuran, 2-methyltetrahydrofuran, dioxane, 1,3-dioxolane, diethylene glycol dimethyl ether, ethylene glycol dimethyl ether, acetonitrile, propionitrile, nitromethane, N,N-dimethylformamide, dimethyl sulfoxide, sulfolane, γ-butyrolactone and the like.

The amount of the non-fluorinated solvent is 30 vol % or less, 20 vol % or less, or 10 vol % or less, with respect to the total volume of the nonaqueous solvent contained in the nonaqueous electrolyte solution. The technology disclosed herein can be implemented in a form where the proportion of the fluorinated solvent in the total volume of the nonaqueous solvent contained in the nonaqueous electrolyte solution is higher than 90 vol %. The proportion of the fluorinated solvent may be 95 vol % or higher, 98 vol % or higher, or even 99 vol % or higher, for instance in terms of increasing oxidation resistance. In some embodiments, a nonaqueous electrolyte solution may include 100 vol % of the nonaqueous solvent contained in the nonaqueous electrolyte solution that is made up of a fluorinated solvent.

Additive A

The nonaqueous electrolyte solution disclosed herein contains, as the additive A, a propylene carbonate derivative represented by General Formula (I) below.

[C3]

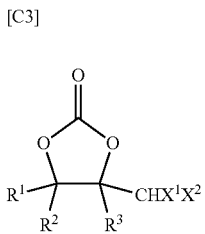

(I)

Wherein $R^1$ to $R^3$ in General Formula (I) (i.e., $R^1$, $R^2$, and $R^3$) are selected, each independently, from the group consisting of hydrogen atoms, fluorine atoms, methyl groups, fluoromethyl groups and difluoromethyl groups, and $X^1$ and $X^2$ are selected, each independently, from the group consisting of hydrogen atoms and fluorine atoms, the at least one from among $R^1$ to $R^3$, and $X^1$ and $X^2$, is a fluorine atom or a group containing a fluorine atom. In the present specification propylene carbonate derivative represented by General Formula (I) encompasses conceptually each geometric isomer of the derivative. The substitution position of $R^1$ and $R^2$ in the propylene carbonate derivative is herein position 1, the substitution position of $R^3$ is position 2 and the substitution position of $X^1$ and $X^2$ is position 3.

In an example of the additive A, all of $R^1$, $R^2$, $R^3$, $X^1$ and $X^2$ are a hydrogen atom or a fluorine atom. Examples of such additive A include for instance 3-fluoropropylene carbonate, 3,3-difluoropropylene carbonate, 1-fluoropropylene carbonate, 1,3-difluoropropylene carbonate, 1,3,3-trifluoropropylene carbonate, 1,1-difluoropropylene carbonate, 1,2-difluoropropylene carbonate, 1,1,3-trifluoropropylene carbonate, 1,2,3-trifluoropropylene carbonate, 1,1,2-trifluoropropylene carbonate, 1,1,2,3-tetrafluoropropylene carbonate, 1,1,3,3-tetrafluoropropylene carbonate, 1,2,3,3-tetrafluoropropylene carbonate, 1,1,2,3,3-pentafluoropropylene carbonate, 2-fluoropropylene carbonate, 2,3-difluoropropylene carbonate, 2,3,3-trifluoropropylene carbonate and the like. In some embodiments, Additive A may include 3-fluoropropylene carbonate and 3,3-difluoropropylene carbonate, in terms of enhancing cycle durability.

In another example of the additive A, all of $R^1$, $R^2$, $X^1$ and $X^2$ are a hydrogen atom or a fluorine atom, and $R^3$ is a methyl group, a fluoromethyl group or a difluoromethyl group. Examples of such additive A include for instance 3-fluoro-2-methyl propylene carbonate, 3,3-difluoro-2-methyl propylene carbonate, 1-fluoro-2-methyl propylene carbonate, 1,3-difluoro-2-methyl propylene carbonate, 1,3,3-trifluoro-2-methyl propylene carbonate, 1,1-difluoro-2-methyl propylene carbonate, 1,1,3-trifluoro-2-methyl propylene carbonate, 1,1,3,3-tetrafluoro-2-methyl propylene carbonate, 3-fluoro-2-(fluoromethyl) propylene carbonate, 3,3-difluoro-2-(fluoromethyl) propylene carbonate, 1-fluoro-2-(fluoromethyl) propylene carbonate, 1,3-difluoro-2-(fluoromethyl) propylene carbonate, 3-fluoro-2-(difluoromethyl) propylene carbonate, 3,3-difluoro-2-(difluoromethyl) propylene carbonate, 1-fluoro-2-(difluoromethyl) propylene carbonate, 1,3-difluoro-2-(difluoromethyl) propylene carbonate and the like.

Other examples of the additive A include instances where $R^1$ is a methyl group, a fluoromethyl group or a difluoromethyl group, and all of $R^2$, $R^3$, $X^1$ and $X^2$ are a hydrogen atom or a fluorine atom. Examples of such additive A include for instance 3-fluoro-1-methyl propylene carbonate, 3,3-difluoro-1-methyl propylene carbonate, 1-fluoro-1-methyl propylene carbonate, 1,3-difluoro-1-methyl propylene carbonate, 1,3,3-trifluoro-1-methyl propylene carbonate, 2-fluoro-1-methyl propylene carbonate, 2,3-difluoro-1-methyl propylene carbonate, 2,3,3-trifluoro-1-methyl propylene carbonate, 3-fluoro-1-(fluoromethyl) propylene carbonate, 3,3-difluoro-1-(fluoromethyl) propylene carbonate, 1-fluoro-1-(fluoromethyl) propylene carbonate, 1,3-difluoro-1-(fluoromethyl) propylene carbonate, 2-fluoro-1-(fluoromethyl) propylene carbonate, 2,3-difluoro-1-(fluoromethyl) propylene carbonate, 3-fluoro-1-(difluoromethyl) propylene carbonate, 3,3-difluoro-1-(difluoromethyl) propylene carbonate, 1-fluoro-1-(difluoromethyl) propylene carbonate, 1,3-difluoro-1-(difluoromethyl) propylene carbonate, 2-fluoro-1-(difluoromethyl) propylene carbonate, 2,3-difluoro-1-(difluoromethyl) propylene carbonate and the like.

Other examples of the additive A include instances where $R^1$ and $R^2$ are a methyl group, a fluoromethyl group or a difluoromethyl group, and all of $R^3$, $X^1$ and $X^2$ are a hydrogen atom or a fluorine atom. Examples of such additive A include for instance 3-fluoro-1,1-dimethyl propylene carbonate, 3,3-difluoro-1,1-dimethyl propylene carbonate, 2-fluoro-1,1-dimethyl propylene carbonate, 2,3-difluoro-1,1-dimethyl propylene carbonate, 2,3,3-trifluoro-1,1-dimethyl propylene carbonate, 3-fluoro-1,1-bis(fluoromethyl) propylene carbonate, 3,3-difluoro-1,1-bis(fluoromethyl) propylene carbonate, 2-fluoro-1,1-bis(fluoromethyl) propylene carbonate, 2,3-difluoro-1,1-bis(fluoromethyl) propylene carbonate, 3-fluoro-1,1-bis(difluoromethyl) propylene carbonate, 3,3-difluoro-1,1-bis(difluoromethyl) propylene carbonate, 2-fluoro-1,1-bis(difluoromethyl) propylene carbonate, 2,3-difluoro-1,1-bis(difluoromethyl) propylene carbonate, 3-fluoro-1-fluoromethyl-1-methyl propylene carbonate, 3-fluoro-1-difluoromethyl-1-methyl propylene carbonate and the like.

Other examples of the additive A include instances where all of $R^1$, $R^2$ and $R^3$ are a methyl group, a fluoromethyl group or a difluoromethyl group, and both $X^1$ and $X^2$ are a hydrogen atom or a fluorine atom. Examples of such additive A include for instance 3-fluoro-1,1,2-trimethyl propylene carbonate, 3,3-difluoro-1,1,2-trimethyl propylene carbonate, 3-fluoro-1,1,2-tris(fluoromethyl) propylene carbonate, 3,3-difluoro-1,1,2-tris(fluoromethyl) propylene carbonate, 3-fluoro-1,1,2-tris(difluoromethyl) propylene carbonate, 3,3-difluoro-1,1,2-tris(difluoromethyl) propylene carbonate, 3-fluoro-1-fluoromethyl-1,2-dimethyl propylene carbonate, 3-fluoro-1-difluoromethyl-1,2-dimethyl propylene carbonate, 3-fluoro-1,2-bis(fluoromethyl)-1-methyl propylene carbonate and the like.

Although not particularly limited thereto, the concentration (content) $C_A$ of the additive A can be set to be 0.0001 mol/L or higher. From the viewpoint of enhancing cycle durability, the concentration $C_A$ of the additive A can be set to 0.0005 mol/L or higher, 0.001 mol/L or higher, or even 0.002 mol/L or higher. The above concentration $C_A$ may be for instance 0.1 mol/L or higher, or 1 mol/L or higher. The upper limit of the concentration $C_A$ of the additive A per 1 L of the nonaqueous electrolyte solution is not particularly restricted, but the upper limit of the concentration $C_A$ may be set to 15 mol/L or less, 10 mol/L or less, or even 5 mol/L or less, for instance in terms of suppressing rises in resistance. In some embodiments, the concentration $C_A$ of the additive A per 1 L of the nonaqueous electrolyte solution can be set to 0.001 mol/L to 3 mol/L, for instance to 0.025 mol/L to 2.5 mol/L, or even from 0.025 mol/L to 1 mol/L.

Additive B

The nonaqueous electrolyte solution disclosed herein further contains additive B represented by General Formula (II).

[C4]

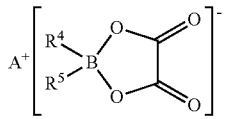

(II)

Wherein $R^4$ and $R^5$ in General Formula (II) are selected, each independently, from among halogen atoms and perfluoroalkyl groups, and $A^+$ is a cation.

The type of cation ($A^+$) in the additive B is not particularly limited and may be an organic cation or an inorganic cation. Specific examples of inorganic cations include for instance cations of alkali metals such as Li, Na and K; cations of alkaline earth metals such as Be, Mg and Ca; cations of metals such as Ag, Zn, Cu, Co, Fe, Ni, Mn, Ti, Pb, Cr, V, Ru and Y, lanthanoids and actinoids; and protons. Examples of organic cations may include for instance tetraalkylammonium ions such as tetrabutylammonium ions, tetraethylammonium ions and tetramethylammonium ions; trialkylammonium ions such as triethylmethylammonium ions and triethylammonium ions; as well as pyridinium ions, imidazolium ions, tetraethylphosphonium ions, tetramethylphosphonium ions, tetraphenylphosphonium ions, triphenylsulfonium ions, triethylsulfonium ions and the like. In some embodiments, the cation in Additive B may include one or more than one of Li ions, tetraalkylammonium ions, and protons.

In the additive B, substituents $R^4$ and $R^5$ on the boron atom can be a halogen atom or a perfluoroalkyl group having 1 to 10, from 1 to 6, or even from 1 to 3 carbon atoms. Herein $R^4$ and $R^5$ may be linear or branched. Further, $R^4$ and $R^5$ may be identical or different. Examples of halogen atoms include for instance fluorine atoms (F), chlorine atoms (Cl) and bromine atoms (Br). In some embodiments, the halogen atoms may be fluorine atoms. Examples of perfluoroalkyl groups having 1 to 10 carbon atoms include for instance perfluoromethyl groups, perfluoroethyl groups, n-perfluoropropyl groups, perfluoroisopropyl groups, n-perfluorobutyl groups, perfluoroisobutyl groups, sec-perfluorobutyl groups, t-perfluorobutyl groups, n-perfluoropentyl groups, perfluoropentyl groups, perfluorohexyl groups, perfluoroheptyl groups, perfluorooctyl groups and the like.

In one example of the additive B, both $R^4$ and $R^5$ are halogen atoms and the cation ($A^+$) is a Li ion. Examples of such additive B include for instance lithium difluorooxalatoborate (LiDFOB), lithium dichlorooxalatoborate, lithium dibromooxalatoborate and the like. In some embodiments, the additive B may be lithium difluorooxalatoborate, which may improve performance in terms of enhancing cycle durability.

Other examples of the additive B include instances where both $R^4$ and $R^5$ are a perfluoroalkyl group having 1 to 10 carbon atoms, and the cation ($A^+$) is a Li ion. Examples of such additive B include for instance lithium di(perfluoromethyl)oxalatoborate, lithium di(perfluoroethyl)oxalatoborate, lithium di(perfluoropropyl)oxalatoborate, lithium di(perfluorobutyl)oxalatoborate and the like.

Other examples of the additive B include instances where one from among $R^4$ and $R^5$ is a halogen atom and the other is a perfluoroalkyl group having 1 to 10 carbon atoms, and the cation ($A^+$) is a Li ion. Examples of such additive B include for instance lithium fluoro(perfluoromethyl)oxalatoborate, lithium fluoro(perfluoroethyl)oxalatoborate, lithium fluoro(perfluoropropyl)oxalatoborate, lithium fluoro (perfluorobutyl)oxalatoborate and the like.

Although not particularly limited thereto, the concentration (content) $C_B$ of the additive B can be set to be 0.0001 mol/L or higher. From the viewpoint of enhancing cycle durability, the concentration $C_B$ of the additive B may be set to 0.0005 mol/L or higher, 0.001 mol/L or higher, or even 0.002 mol/L or higher. The above concentration $C_B$ may be for instance 0.003 mol/L or higher, or even 0.005 mol/L or higher. The upper limit of the concentration $C_B$ of the additive B per 1 L of the nonaqueous electrolyte solution is not particularly limited, but ordinarily upper limit may be set to 3 mol/L or less, 1 mol/L or less, or even 0.5 mol/L or less, for instance in terms of suppressing rises in resistance. In some embodiments, the concentration $C_B$ of the additive B per 1 L of the nonaqueous electrolyte solution can be set to 0.001 mol/L to 0.5 mol/L, for instance 0.025 mol/L to 0.1 mol/L.

The molar concentration $C_A$ of the additive A is higher than the molar concentration $C_B$ of the additive B (i.e. $C_A > C_B$) from the viewpoint of better bringing out the effect derived from using concomitantly additive A and additive B. A ratio ($C_A/C_B$) of the molar concentration $C_A$ of the additive A with respect to the molar concentration $C_B$ of the additive B may be about 1 or higher, for instance 2 or higher, or even 5 or higher. For instance in terms of maintaining low resistance, the above molar concentration ratio $C_A/C_B$ may be set to about 30 or less, 25 or less, 20 or less, 15 or less, or even 10 or less. For instance, a nonaqueous electrolyte solution having a molar concentration ratio $C_A/C_B$ of 1 to 30 (in particular 1 to 5) is appropriate from the viewpoint of combining low resistance with enhanced cycle durability.

The nonaqueous electrolyte solution disclosed herein contains the additive A and the additive B at a specific concentration ratio. The cycle durability of a battery constructed using a nonaqueous electrolyte solution containing a fluorinated solvent can be effectively enhanced by using a combination of the additive A and additive B, at a specific concentration ratio, in a nonaqueous electrolyte solution. Conceivable underlying reasons for such an effect include, although not meant to be limited thereto, for instance the following. Specifically, fluorinated solvents have low reduction resistance, and accordingly a dense coating film has to be formed that exhibits high electron insulating properties and in which degradation can be suppressed, but the additive B does not dissolve readily in fluorinated solvents, and a sufficient coating film is not formed readily on a negative electrode surface. Also, it is difficult to form a good coating film (coating film having high electron insulating properties and in which degradation can be suppressed) using the additive A singly. In a battery in which the additive A and the additive B are used combined at a specific concentration ratio, by contrast, the additive A and the additive B decompose together with the electrolyte solution components (fluorinated solvent, supporting salt and so forth) for instance during initial charging, and a mixed coating film made up of decomposition products of the foregoing, i.e. a mixed coating film of the additive A and the additive B covers the surface of an electrode (typically a negative electrode), so that as a result further decomposition of electrolyte solution components is suppressed, which can contribute to enhancing the performance of the battery. Such a mixed coating film has higher electron insulating properties and is denser than a coating film formed when using the additive A or the additive B singly, and hence it becomes possible to suppress effectively further decomposition of electrolyte solution components. It is deemed that capacity degradation and increases in resistance after endurance of the battery can be effectively improved upon as a result.

Studies by the inventors on the basis of the test examples described below have revealed that a higher performance improving effect is achieved when the additive A and additive B are used in combination at a specific concentration ratio, than when the additive A and additive B are each used singly. In other words, a nonaqueous electrolyte solution that allows enhancing cycle durability can be provided by using additive A and additive B in combination, at a specific concentration ratio, by virtue of the synergy gained from such a combination.

The nonaqueous electrolyte solution disclosed herein may contain a coating film forming agent (hereafter third additive) other than the additive A and additive B. Examples of such a third additive include for instance vinylene carbonate (VC), monofluoroethylene carbonate (MFEC), 1,3-propane sultone (PS) and the like. The amount of the third additive is for instance set to 50 mass % or less (for instance 0 mass % to 50 mass %), 35 mass % or less, 20 mass % or less, or even 10 mass % or less, with respect to the total mass of the coating film forming agent contained in the nonaqueous electrolyte solution. The technology disclosed herein can be implemented in a form where substantially no third additive is present.

The nonaqueous electrolyte solution disclosed herein is thus excellent in oxidation resistance and has good cycle durability, and accordingly it can be used as a constituent element of lithium ion secondary batteries of such a form. A lithium ion secondary battery can be constructed in accordance with conventional processes except that a fluorine-based solvent is used as a nonaqueous solvent and that the additive A and additive B disclosed herein are used. Although not meant to be particularly limited thereto, an example of the lithium ion secondary battery schematically illustrated in FIG. 1, will be explained as the schematic configuration of a secondary battery provided with a non-aqueous electrolyte solution according to the present disclosure, but the scope of application of the present disclosure is not meant to be limited to this example.

A lithium ion secondary battery 100 illustrated in FIG. 1 has a configuration in which a wound electrode body 80, of a fo in resulting from winding flatly of a positive electrode sheet 10 and a negative electrode sheet 20 across a separator sheet 40, is accommodated in a box-shaped battery case 50 together with a nonaqueous electrolyte solution not shown.

The battery case 50 is provided with a flat rectangular parallelepiped shape (box type) battery case body 52 the top end of which is open, and with a lid body 54 that plugs the opening of the case body 52. A comparatively light metal (for instance, aluminum or an aluminum alloy) can be used as the material of the battery case 50. A positive electrode terminal 70 for external connection, electrically connected to the positive electrode of the wound electrode body 80, and a negative electrode terminal 72 electrically connected to the negative electrode of the wound electrode body 80, are provided on the top face (i.e. lid body 54) of the battery case 50. The lid body 54 is provided with a safety valve 55 for discharging, out of the case 50, gas that is generated inside the battery case 50, similarly to the battery cases of conventional lithium ion secondary batteries.

The wound electrode body 80 of flat shape is accommodated, together with the nonaqueous electrolyte solution (not shown) described above, inside the battery case 50. The wound electrode body 80 is provided with an elongated sheet-shaped positive electrode (positive electrode sheet) 10 and an elongated sheet-shaped negative electrode (negative electrode sheet) 20.

Positive Electrode

The positive electrode sheet 10 is provided with an elongated positive electrode collector and a positive electrode active material layer 14 formed along the longitudinal direction on at least one surface or both surfaces of the positive electrode collector. Such a positive electrode sheet 10 can be produced for instance by applying a composition, resulting from dispersing a forming component of a positive electrode active material layer in an appropriate solvent (for instance N-methyl-2-pyrrolidone), onto the surface of the positive electrode collector, and drying the composition. The forming component of the above positive electrode active material layer can contain a positive electrode active material, and also for instance a conductive material and a binder (binding agent) that are utilized as needed. A metal of good conductivity (for instance, aluminum, nickel, titanium, stainless steel or the like) can be used as the positive electrode collector.

The operating upper limit potential of the positive electrode of the lithium ion secondary battery disclosed herein is 4.3 V or higher, 4.35 V or higher, 4.6 V or higher, or even 4.7 V or higher with reference to metallic lithium within a range of SOC (State Of Charge) of 0% to 100%. The highest operating potential between SOC 0% to 100% occurs generally at SOC 100%, and accordingly the operating upper limit potential of the positive electrode can be grasped ordinarily through the operating potential of the positive electrode at SOC 100% (i.e. in a full charge state). The technology disclosed herein can be used in a lithium ion secondary battery in which the operating upper limit potential of the positive electrode lies in the range of 4.3 V to 5.5 V (for instance 4.7 V to 5.2 V) with reference to metallic lithium, within a range of SOC 0% to 100%.

The positive electrode exhibiting such an operating upper limit potential can be realized by using a positive electrode active material having a highest value of operating potential of 4.3 V or higher (with respect to $Li/Li^+$), for a SOC in the range of 0% to 100%. Among the foregoing there is used a positive electrode active material the operating potential of which, at SOC 100%, exceeds 4.3 V, 4.5 V or higher, 4.6 V or higher, or even 4.9 V or higher, with reference to metallic lithium. Yet higher energy density can be realized by using a positive electrode active material having the above operating potential. Side reactions with a positive electrode can be suitably suppressed through the use, in the nonaqueous electrolyte solution, of the fluorinated solvent, also in a positive electrode at such high potential.

The operating potential of a positive electrode active material can be measured for instance as follows. Specifically, firstly there is constructed a tri-polar cell using a working electrode (WE) in the form of a positive electrode containing a positive electrode active material, as the measurement target, as well as a counter electrode (CE) and metallic lithium as a reference electrode (RE), and a nonaqueous electrolyte solution. Next, the SOC of the cell is adjusted from 0% to 100% in increments of 5%, on the basis of the theoretical capacity of the cell. Adjustment of the SOC can be accomplished through constant-current charging across the WE-CE, using for instance an ordinary charging and discharging device or a potentiostat. The cell having been adjusted to a given SOC state is allowed to stand for 1 hour, after which potential across the WE-RE is measured, and the potential is taken as the operating potential (with respect to Li/Li$^+$) of the positive electrode active material at the respective SOC state.

Examples of positive electrode active materials that can suitably realize such high potential include for instance lithium-manganese complex oxides of spinel structure. Some embodiments among the foregoing include lithium-nickel-manganese complex oxides of spinel structure having Li, Ni and Mn as constituent metal elements. A more specific example is a lithium-nickel-manganese complex oxide having a spinel structure and represented by General Formula (III).

$$Li_x(Ni_yMn_{2-y-z}Me^1{}_z)O_{4+\alpha} \qquad (III)$$

Wherein Me$^1$ can be any transition metal element or typical metal element (for instance one, two or more elements selected from among Fe, Ti, Co, Cu, Cr, Zn and Al), other than Ni and Mn. Alternatively, Me$^1$ may be a metalloid element (for instance one, two or more elements selected from among B, Si and Ge) or a non-metal element. Further, x is $0.8 \leq x \leq 1.2$; y is $0<y$; z is $0 \leq z$; there holds y+z<2, or even y+z$\leq$1; and $\alpha$ is a value such that a charge neutral condition is satisfied with $-0.2 \leq \alpha \leq 0.2$. In some embodiments, y is $0.2 \leq y \leq 1.0$, such as $0.4 \leq y \leq 0.6$, for instance $0.45 \leq y \leq 0.55$; and z is $0 \leq z < 1.0$ (for instance $0 \leq z \leq 0.3$). Examples of the lithium-nickel-manganese complex oxide represented by the general formula above include for instance LiNi$_{0.5}$Mn$_{1.5}$O$_4$ and the like. Such lithium-nickel-manganese complex oxides of spinel structure can contribute to increasing energy density. Whether a compound (oxide) has a spinel structure or not can be determined for instance by X-ray structural analysis (preferably single-crystal X-ray structural analysis). Specifically, the presence or absence of a spinel structure can be determined by X-ray diffraction measurements using CuK$\alpha$ rays.

Other examples of the positive electrode active material disclosed herein include for instance lithium transition metal complex oxides, typically of layered structure, represented by general formula LiMe$^2$O$_2$. Herein Me$^2$ includes at least one transition metal element such as a Ni, Co, Mn and the like, and can further include other metal elements or non-metal elements. Such a layered-structure lithium transition metal complex oxide can contribute to increasing the capacity of the battery.

Other examples of the positive electrode active material disclosed herein include for instance lithium transition metal compounds (phosphate salts) of olivine structure represented by foiliiula LiMe$^3$PO$_4$. Herein Me$^3$ includes at least one transition metal element such as Mn, Fe, Co and the like, and can further include other metal elements or non-metal elements. Examples include for instance LiMnPO$_4$, LiFePO$_4$, LiCoPO$_4$ and the like.

Other examples of the positive electrode active material disclosed herein include of solid solutions of LiMe$^2$O$_2$ and Li$_2$Me$^4$O$_3$. Herein LiMe$^2$O$_2$ represents a composition represented by the general formula above. Further, Me$^4$ in Li$_2$Me$^4$O$_3$ includes at least one transition metal element such as Mn, Fe, Co and the like, and can further include other metal elements or non-metal elements. Examples include for instance Li$_2$MnO$_3$ or the like. Examples of the above solid solution include for instance a solid solution represented by 0.5LiNi$_{1/3}$Co$_{1/3}$Mn$_{1/3}$O$_2$-0.5Li$_2$MnO$_3$.

The positive electrode active material described above can be used singly or as a combination of two or more types. Among the foregoing, in some embodiments, the positive electrode active material contains a lithium-nickel-manganese complex oxide of spinel structure represented by General Formula (III) in a proportion of 50 mass % or higher, such as 50 mass % to 100 mass %, for instance 70 mass % to 100 mass %, or even 80 mass % to 100 mass % with respect to the total positive electrode active material that is used. In some embodiments, the positive electrode active material is substantially made up of only a lithium-nickel-manganese complex oxide of spinel structure.

In the technology disclosed herein the positive electrode active material is of particulate form having an average particle size of 1 μm to 20 μm, or from 2 μm to 15 μm. Unless otherwise specified the term "average particle size" denotes a particle size (D$_{50}$, also referred to as median size) corresponding to a cumulative frequency of 50 vol %, from the side of microparticles of small particle size in a volume-based particle size distribution based on a laser diffraction/light scattering method.

Other Constituent Components of the Positive Electrode Active Material Layer

Besides the positive electrode active material, the positive electrode active material layer can contain additives such as a conductive material and a binder (binding material). A conductive powder material such as carbon powder or carbon fibers may be used as the conductive material. Examples of carbon powder include for instance various carbon blacks (CB) for instance acetylene black (AB).

Examples of the binder include various polymer materials. For instance a water-soluble or water-dispersible polymer material can be used in a case where a positive electrode active material layer is formed using an aqueous composition (composition in which a dispersion medium is water or a mixed solvent having water as a main component). Examples of water-soluble and water-dispersible polymer materials include for instance cellulosic polymers such as carboxymethyl cellulose (CMC); fluororesins such as polytetrafluoroethylene (PTFE); and rubbers such as styrene butadiene rubber (SBR). Alternatively, a polymer material, for instance a halogenated vinyl resin such as polyvinylidene fluoride (PVdF); or a polyalkylene oxide such as polyethylene oxide (PEO) can be used in a case where the positive electrode active material layer is formed using a solvent-based composition (composition in which dispersion medium is mainly an organic solvent). Such a binder can be used singly or as a combination of two or more types. In addition to being used as a binder, the polymer materials exemplified above may be used as a thickener, a dispersant or as some other additive.

The proportion of the positive electrode active material in the positive electrode active material layer as a whole is about 50 mass % or more, such as 50 mass % to 95 mass %. In some embodiments, the proportion is set to 70 mass % to 97 mass %, such as from 75 mass % to 95 mass %. If a conductive material is used, the proportion of the conductive material in the positive electrode active material layer as a whole can be set to about 2 mass % to 20 mass %. In some embodiments, the proportion is set to about 2 mass % to 15 mass %. If a binder is used, the proportion of the binder in the positive electrode active material layer as a whole can be set to about 0.5 mass % to 10 mass, such as from about 1 mass % to 5 mass %.

Negative Electrode

The negative electrode sheet 20 is provided with an elongated negative electrode collector and with a negative electrode active material layer 24 formed along the longitudinal direction on at least one surface or both surfaces of the negative electrode collector. Such a negative electrode sheet 20 can be produced for instance by applying, onto the surface of the negative electrode collector, a composition resulting from dispersing a forming component of a negative electrode active material layer in an appropriate solvent (for instance water), and by drying the composition. The forming component of the negative electrode active material layer can contain a negative electrode active material, and a binder and so forth that are used as needed. A conductive material made up of a metal of good conductivity (for instance, copper, nickel, titanium, stainless steel or the like) can be used as the negative electrode collector.

Herein, one, two, or more substances that are utilized in lithium ion secondary batteries can be used, without particular limitations, as the negative electrode active material. Examples of the negative electrode active material include for instance carbon materials. Examples of carbon materials include for instance graphite carbon (graphite), amorphous carbon, and the like. A particulate carbon material (carbon particles) containing a graphite structure (layered structure) at least partially may be used in some embodiments. In other embodiments, a carbon material having natural graphite as a main component may be used among the foregoing. The above natural graphite can be obtained through spheroidization of scaly graphite. A carbonaceous powder resulting from coating the surface of graphite with amorphous carbon may also be used herein. As the negative electrode active material there can be alternatively used single species, alloys and compounds of metal oxide materials such as silicon oxide, titanium oxide, vanadium oxide and lithium-titanium composite oxides (LTO); metal nitride materials such as lithium nitride, lithium-cobalt complex nitrides, lithium-nickel complex nitrides; and also, silicon materials, tin materials and the like, as well as composite materials in which the foregoing materials are used concomitantly. A negative electrode active material having a reduction potential (with respect to $Li/Li^+$) of about 0.5 V or less, such as 0.2 V or less, or even 0.1 V or less, may be used among the foregoing. Higher energy density can be realized by using a negative electrode active material having the above reduction potential. Examples of materials that can yield such low potential include for instance natural graphite-based carbon materials. In the technology disclosed herein the negative electrode active material may be of particulate form having an average particle size of 10 μm to 30 μm, such as from 15 μm to 25 μm.

Other Constituent Components of the Negative Electrode Active Material Layer

Besides the negative electrode active material, the negative electrode active material layer can contain additives such as a binder (binding agent), a thickener and the like. The same materials explained regarding the positive electrode active material layer can be used as the binder and the thickener that are used in the negative electrode active material layer.

The proportion of the negative electrode active material in the negative electrode active material layer as a whole exceeds about 50 mass %, such as from about 80 mass % to 99.5 mass %, or even 90 mass % to 99 mass %. The proportion of binder in the negative electrode active material layer as a whole may be about 0.5 mass % to 5 mass %, such as from mass % to 2 mass %. The proportion of thickener in the negative electrode active material layer as a whole may be about 0.5 mass % to 5 mass %, such as from 1 mass % to 2 mass %.

Two separators (separator sheets) 40 having an elongated sheet shape are disposed, between the positive electrode active material layer 14 and the negative electrode active material layer 24, as an insulating layer for preventing direct contact between the foregoing. A porous sheet made of a resin such as polyethylene (PE), polypropylene (PP), polyester, cellulose, polyamide or the like, or a nonwoven fabric or the like, can be used as the separator sheets 40.

The wound electrode body 80 can be produced for instance by winding, in the longitudinal direction, a stack resulting from sequentially superimposing the positive electrode sheet 10, a separator sheet 40, the negative electrode sheet 20 and a separator sheet 40, and by pressing and squashing the resulting wound body from the sides, to form the stack into a flat shape.

A wound core portion in which the positive electrode active material layer 14 formed on the surface of the positive electrode collector and the negative electrode active material layer 24 formed on the surface of the negative electrode collector are superimposed and densely overlaid on each other is formed at a central portion of the wound electrode body 80 in the width direction, defined as the direction from one end of the wound electrode body 80 towards the other end in the winding axis direction. A positive electrode active material layer non-forming portion of the positive electrode sheet 10 and a negative electrode active material layer non-forming portion of the negative electrode sheet 20 jut outward of the wound core portion, on both ends of the wound electrode body 80 in the winding axis direction. A positive electrode power collector plate is attached to the jutting portion on the positive electrode side and a negative electrode power collector plate is attached to the jutting portion on the negative electrode, and the collector plates are electrically connected to the positive electrode terminal 70 and the negative electrode terminal 72, respectively.

Method for Producing a Lithium Ion Secondary Battery

The lithium ion secondary battery 100 having such a configuration can be produced as a result of a battery assembly construction step and an initial charging step.

Battery Assembly Construction Step

In the battery assembly construction step the wound electrode body 80 provided with the positive electrode sheet 10 and the negative electrode sheet 20 is accommodated inside a battery case together with the nonaqueous electrolyte solution, to construct thereby a battery assembly. The term battery assembly denotes a battery having been assembled to the form that precedes the initial charging step in the production processes of the battery. The battery assembly can be constructed for instance by accommodating the wound electrode body 80 inside the battery case 50, through the opening of the battery case 50, attaching the lid body 54 to the opening of the case 50, injecting thereafter a nonaqueous electrolyte through an injection hole, not shown, provided in the lid body 54, and sealing next the injection hole by welding or the like. In this implementation the nonaqueous electrolyte solution accommodated in the battery assembly contains the above fluorinated solvent as the nonaqueous solvent. The nonaqueous electrolyte solution contains the additive A represented by General Formula (I) and the additive B represented by General Formula (II).

Initial Charging Step

In the initial charging step the battery assembly is subjected to initial charging. Typically, an external power source is connected between the positive electrode (positive electrode terminal) and the negative electrode (negative electrode terminal) of the battery assembly, to charge the battery assembly (e.g., by constant-current charging) up to a predetermined voltage range. A good-quality coating film containing components derived from the additive A and the additive B becomes formed as a result on the negative electrode surface.

The voltage during initial charging may be for instance set such that the additive A and the additive B are electrically decomposed. As an example, the negative electrode active material is a carbon material, charging is performed up to a voltage of about 3 V or higher (3.5 V or higher, or even 4.7 V or higher), such as from 4 V to 5 V, across the positive and negative electrode terminals. Such charging may be performed according to a scheme (CC charging) that involves constant-current charging from the start of charging until the battery voltage reaches a predetermined value, or according to a scheme (CC-CV charging) in which constant-voltage charging is performed after the above predetermined voltage has been reached. The charging rate at the time of constant-current charging is ordinarily 1 C or lower, for example from 0.1 C to 0.2 C. Findings by the inventors have revealed that the additive A and the additive B decompose relatively gently when charging is performed at a low rate of 1 C or less. A coating film containing components of the additive A and the additive B is formed, with suitable denseness (for instance, a coating film of low resistance and capable of sufficiently suppressing reactivity with a nonaqueous electrolyte solution), on the surface of the negative electrode. The effect of the present configuration can therefore be brought out to a yet higher level. Charging may be perfoinied once, or twice or more, for instance with intervening discharges.

The lithium ion secondary battery 100 according to the present embodiment can be thus produced in the above manner.

Although the lithium ion secondary battery disclosed herein can be used in various applications, the characterizing feature of the battery is its excellent cycle durability, and hence the battery can be used, by exploiting that characterizing feature, in applications where high performance (for instance long lifespan) is required. Relevant applications include for instance driving power sources that are installed in vehicles such as plug-in hybrid automobiles, hybrid automobiles, electric automobiles and the like. Such secondary batteries can be used in the form of assembled batteries resulting from series and/or parallel connection of a plurality of secondary batteries.

Several examples relating to the present disclosure will be described below, but the disclosure is not intended to be limited to such examples.

Nonaqueous Electrolyte Solution

Example 1

A reference electrolyte solution NA, being a solution containing $LiPF_6$ at a concentration of 1 mol/L in a mixed solvent of trifluoropropylene carbonate (TFPC) and methyl trifluoroethyl carbonate (MTFEC) (volume ratio 30:70), as a fluorinated solvent, was used as an electrolyte solution sample of Example 1.

Example 2

An electrolyte solution sample of Example 2 was obtained by adding 3-fluoropropylene carbonate (FPC: compound where $R^1$, $R^2$ and $R^3$=H, and $R^4$=$CFH_2$ in General Formula (I)), as the additive A, to the reference electrolyte solution NA, to a concentration $C_A$ of 0.5 mol/L.

Example 3

An electrolyte solution sample of Example 3 was obtained by adding lithium difluorooxalatoborate (LiDFOB: compound corresponding to $R^4$ and $R^5$=F, and A=Li in General Formula (II)), as the additive B, to the reference electrolyte solution NA to a concentration $C_B$ of 0.05 mol/L.

Examples 4 to 14

Electrolyte solution samples of Examples 4 to 14 were obtained by adding FPC as the additive A and LiDFOB as the additive B to the reference electrolyte solution NA, to respective predetermined concentrations $C_A$, $C_B$.

Table 1 summarizes the types and concentration $C_A$ of the additive A, the types and concentration $C_B$, as well as the concentration ratio $C_A/C_B$, for the electrolyte solution samples in the various examples.

TABLE 1

| Example | Additive A Type | Additive A Concentration $C_A$ (mol/L) | Additive B Type | Additive B Concentration $C_B$ (mol/L) | Concentration ratio CA/CB | Capacity retention rate (%) | Resistance (Ω) |
|---|---|---|---|---|---|---|---|
| 1 | — | — | — | — | — | 68 | 1.4 |
| 2 | FPC | 0.5 | — | — | — | 63 | 1.6 |
| 3 | — | — | LiDFOB | 0.05 | — | 77 | 1.3 |
| 4 | FPC | 0.025 | LiDFOB | 0.05 | 0.5 | 76 | 1.3 |
| 5 | FPC | 0.5 | LiDFOB | 0.01 | 50 | 70 | 1.6 |
| 6 | FPC | 3 | LiDFOB | 0.1 | 30 | 88 | 2 |
| 7 | FPC | 0.05 | LiDFOB | 0.05 | 1 | 91 | 1.3 |
| 8 | FPC | 0.1 | LiDFOB | 0.05 | 2 | 91 | 1.3 |
| 9 | FPC | 0.025 | LiDFOB | 0.025 | 1 | 87 | 1.4 |

TABLE 1-continued

| | | Additive A | | Additive B | Concentration ratio CA/CB | Capacity retention rate (%) | Resistance (Ω) |
|---|---|---|---|---|---|---|---|
| Example | Type | Concentration $C_A$ (mol/L) | Type | Concentration $C_B$ (mol/L) | | | |
| 10 | FPC | 0.5 | LiDFOB | 0.025 | 20 | 88 | 1.5 |
| 11 | FPC | 0.5 | LiDFOB | 0.05 | 10 | 90 | 1.4 |
| 12 | FPC | 0.5 | LiDFOB | 0.1 | 5 | 89 | 1.4 |
| 13 | FPC | 1 | LiDFOB | 0.1 | 10 | 89 | 1.5 |
| 14 | FPC | 2.5 | LiDFOB | 0.1 | 25 | 90 | 1.7 |

Production of Lithium Ion Secondary Batteries

Lithium ion secondary batteries for evaluation were produced in the manner described below, using the respective electrolyte solutions produced in Examples 1 to 14.

The positive electrode of the lithium ion secondary batteries was produced as follows. Specifically, a composition for forming a positive electrode active material layer was prepared by mixing a spinel structure lithium-nickel-manganese complex oxide ($LiNi_{0.5}Mn_{1.5}O_4$), as a positive electrode active material, acetylene black (AB) as a conductive material, and PVdF as a binder, to a mass ratio of the foregoing materials of 87:10:3. This composition was applied onto one side of an aluminum foil (positive electrode collector), and was dried, followed by roll-pressing to a density of the positive electrode active material layer of 2.3 g/cm$^3$, to thereby obtain a positive electrode sheet having a positive electrode active material layer formed on the positive electrode collector.

The negative electrode of the lithium ion secondary batteries was produced as follows. Specifically, a composition for forming a negative electrode active material layer was prepared by mixing, in water, natural graphite (average particle size 10 μm, surface area $D_{50}$=4.8 m$^2$/g) as a negative electrode active material, SBR as a binder and CMC as a thickener to a mass ratio of the foregoing materials of 98:1:1. This composition was applied onto one side of a copper foil (negative electrode collector), and was dried, followed by roll-pressing to thereby obtain a negative electrode sheet having a negative electrode active material layer formed on a negative electrode collector. The coating amounts of the composition for forming a positive electrode active material layer and of the composition for forming a negative electrode active material layer were adjusted to yield a ratio by weight of 2:1 of the positive electrode active material and the negative electrode active material.

As a separator there was prepared a separator made up of a base material of a micro-porous membrane (PP/PE/PP membrane) having a three-layer structure of polypropylene/polyethylene/polypropylene.

A laminate cell was constructed using the positive electrode, negative electrode and separator having been prepared above. Specifically, electrode bodies were produced by superimposing the produced positive and electrode negative electrode, with the separator interposed in between, in such a manner that the active material layers of the electrodes opposed each other. Next, the electrode bodies were accommodated in laminate-made bag-like battery containers, together with the electrolyte solution samples of the examples, to construct respective battery assemblies.

Each battery assembly was conditioned by repeating thrice an operation that involved charging at C/3 constant current, at a temperature of 25° C., until 4.9 V was reached, followed by a 10-minute pause, with subsequent discharge at C/3 constant current down to 3.5 V, followed in turn by a 10-minute pause. Respective evaluation cells (laminate cells) of Examples 1 to 14 were constructed in this manner.

Measurement of Rated Capacity

Each evaluation cell was charged at C/3 constant current, at a temperature of 25° C., until 4.9 V was reached, with subsequent charging for 2.5 hours at the same voltage. After a 10-minute pause, the cell was discharged at a C/3 rate down to 3 V, with subsequent discharge for 2 hours at the same voltage; the discharge capacity measured at the time of this discharge was taken herein as the initial capacity (rated capacity).

Measurement of Initial Resistance

The evaluation cells of the examples, having been adjusted to SOC 60% (charge state of about 60% of the rated capacity) were discharged at rates of 1 C, 3 C, 5 C and 10 C, for 10 seconds, and the voltage drops during that lapse of time were measured. Internal resistance was calculated by dividing the measured voltage drop amount by the current value during discharge, and the calculated internal resistance was taken as the initial resistance. The results are given in Table 1 in the column "Resistance".

Cycle Endurance Test

The evaluation cells of the examples were placed in a thermostatic bath at about 60° C., and were subjected to a cycle endurance test that involved repeating continuously 200 charge and discharge cycles, each including charging at 2 C of constant current up to 4.9 V, followed by discharge at 2 C of constant current down to 3.5 V.

Capacity retention rates were calculated on the basis of the initial capacity before the cycle endurance test and the battery capacity after the cycle endurance test. The battery capacity after the cycle endurance test was measured in accordance with the same procedure as that of the initial capacity described above. The capacity retention rate was worked out as "battery capacity after cycle endurance test/initial capacity before cycle endurance test"×100. The results are given in Table 1 in the column "Capacity retention rate".

As Table 1 reveals, the evaluation cell of Example 2, which utilized a nonaqueous electrolyte solution having only FPC added thereto, exhibited a drop in capacity retention rate after the endurance test as compared with Example 1, in which a nonaqueous electrolyte solution without additive was used. The evaluation cell of Example 3, in which there was used a nonaqueous electrolyte solution having only LiDFOB added thereto, exhibited a slight improvement in capacity retention rate as compared with Example 1, but the value of capacity retention rate was lower than 80%. The capacity retention rates of the evaluation cells of Examples 4 and 5, in which FPC and LiDFOB were used concomitantly and the concentration ratio $C_A/C_B$ was set to 0.05 and 50, exhibited a slight improvement as compared with Example 1, but the values of capacity retention rate were lower than 80%. The evaluation cells of Examples 6 to 14, in which FPC and LiDFOB were used concomitantly and the concentration ratio $C_A/C_B$ was set to 1 to 30, exhibited by contrast good durability in that it was possible to achieve a capacity retention rate of 88% or higher after the endurance test. The above indicated that a high durability enhancing effect can be achieved by using concomitantly the additive A and the additive B, and by setting the concentration ratio $C_A/C_B$ to 1 to 30. The evaluation cells of Examples 5 to 14, in which FPC and LiDFOB were used concomitantly and the concentration ratio $C_A/C_B$ was set to 1 to 25, afforded a lower resistance than that of Example 6, in which FPC and LiDFOB were used concomitantly and the concentration ratio $C_A/C_B$ was set to 30. The concentration ratio $C_A/C_B$ is thus set to 25 or less from the viewpoint of maintaining low resistance.

Examples of the present disclosure have been explained in detail above, but these examples are merely illustrative in nature, and are not meant to limit the scope of the claims. The present disclosure may encompass various modifications and alterations of the above-described examples.

What is claimed is:

1. A nonaqueous electrolyte solution used in a nonaqueous electrolyte secondary battery, comprising:
   a fluorinated solvent;
   an additive A represented by General Formula (I):

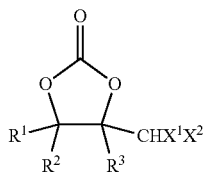

(I)

wherein, $R^1$, $R^2$, and $R^3$ are selected, each independently, from the group consisting of hydrogen atoms, fluorine atoms, methyl groups, fluoromethyl groups and difluoromethyl groups, and $X^1$ and $X^2$ are selected, each independently, from the group consisting of hydrogen atoms and fluorine atoms, where at least one from among $R^1$, $R^2$, $R^3$, $X^1$, and $X^2$ is a fluorine atom or a group comprising a fluorine atom; and an additive B represented by General Formula (II):

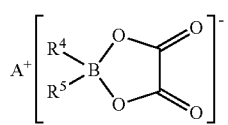

(II)

wherein, $R^4$ and $R^5$ are selected, each independently, from among halogen atoms and perfluoroalkyl groups, and $A^+$ is a cation, wherein a ratio ($C_A/C_B$) of concentration $C_A$ (mol/L) of the additive A and concentration $C_B$ (mol/L) of the additive B in the nonaqueous electrolyte solution lies in a range of 1 to 30.

2. The nonaqueous electrolyte solution according to claim 1, comprising, as the additive A, at least one selected from the group consisting of fluoropropylene carbonate and difluoropropylene carbonate.

3. The nonaqueous electrolyte solution according to claim 1, comprising lithium difluorooxalatoborate as the additive B.

4. The nonaqueous electrolyte solution according to claim 1, further comprising a supporting salt comprising at least one of $LiPF_6$, $LiBF_4$, $LiAsF_6$, $LiCF_3SO_3$, $LiC_4F_9SO_3$, $Li(CF_3SO_2)_2N$, $LiC(CF_3SO_2)_3$, $LiSiF_6$, $LiClO_4$, or combinations thereof.

5. The nonaqueous electrolyte solution according to claim 1, further comprising a coating film forming agent.

6. The nonaqueous electrolyte solution according to claim 5, wherein the coating film forming agent comprises vinylene carbonate, monofluoroethylene carbonate, 1,3-propane sultone, or combinations of these.

7. The nonaqueous electrolyte solution according to claim 1, wherein the fluorinated solvent comprises at least one fluorinated linear carbonate and at least one fluorinated cyclic carbonate.

8. The nonaqueous electrolyte solution according to claim 1, comprising a concentration of Additive A of from 0.001 mol/L to 3 mol/L.

9. The nonaqueous electrolyte solution according to claim 1, wherein:
   the fluorinated solvent comprises trifluoropropylene carbonate and methyl trifluoroethyl carbonate and a volume ratio of trifluoropropylene carbonate to methyl trifluoroethyl carbonate is 30:70;
   Additive A comprises 3-fluoropropylene carbonate and the concentration $C_A$ of Additive A in the nonaqueous electrolyte solution is from 0.5 mol/L to 3 mol/L;
   Additive B comprises lithium difluorooxalatoborate and the concentration CB of Additive B in the nonaqueous electrolyte solution is from 0.025 mol/L to 1 mol/L; and
   the nonaqueous electrolyte solution further comprises a supporting salt comprising $LiPF_6$ and a concentration of the supporting salt in the nonaqueous electrolyte solution is 1 mol/L.

10. The nonaqueous electrolyte solution according to claim 1, wherein a portion of the fluorinated solvent is 95 vol % or higher with respect to 100 vol % of the nonaqueous electrolyte solution.

11. The nonaqueous electrolyte solution according to claim 1, wherein the nonaqueous electrolyte solution consists essentially of the fluorinated solvent, the additive A, and the additive B.

12. A method for producing a nonaqueous electrolyte secondary battery,
the method comprising:
    constructing a battery assembly by accommodating a positive electrode and a negative electrode inside a battery case, together with a nonaqueous electrolyte solution; and
    subjecting the battery assembly to an initial charging treatment,
    wherein the nonaqueous electrolyte solution accommodated in the battery assembly includes:
    a fluorinated solvent;
    an additive A represented by General Formula (I):

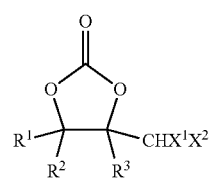

(I)

wherein, $R^1$, $R^2$, and $R^3$ are selected, each independently, from the group consisting of hydrogen atoms, fluorine atoms, methyl groups, fluoromethyl groups and difluoromethyl groups, and $X^1$ and $X^2$ are selected, each independently, from the group consisting of hydrogen atoms and fluorine atoms, where at least one from among $R^1$, $R^2$, $R^3$, $X^1$, and $X^2$ is a fluorine atom or a group comprising a fluorine atom; and an additive B represented by General Formula (II):

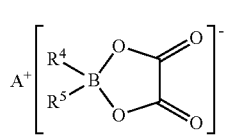

(II)

wherein, $R^4$ and $R^5$ are selected, each independently, from among halogen atoms and perfluoroalkyl groups, and $A^+$ is a cation, and wherein a ratio ($C_A/C_B$) of concentration $C_A$ (mol/L) of the additive A and concentration $C_B$ (mol/L) of the additive B in the nonaqueous electrolyte solution lies in a range of 1 to 30.

13. The method for producing a nonaqueous electrolyte secondary battery according to claim 12, wherein the nonaqueous electrolyte solution comprises, as the additive A, at least one selected from the group consisting of fluoropropylene carbonate and difluoropropylene carbonate.

14. The method for producing a nonaqueous electrolyte secondary battery according to claim 12, wherein the nonaqueous electrolyte solution comprises lithium difluorooxalatoborate, as the additive B.

15. The method for producing a nonaqueous electrolyte secondary battery according to claim 12, wherein the nonaqueous electrolyte solution further comprises a supporting salt comprising at least one of $LiPF_6$, $LiBF_4$, $LiAsF_6$, $LiCF_3SO_3$, $LiC_4F_9SO_3$, $Li(CF_3SO_2)_2N$, $LiC(CF_3SO_2)_3$, $LiSiF_6$, $LiClO_4$, or combinations thereof.

16. The method for producing a nonaqueous electrolyte secondary battery according to claim 12, wherein the nonaqueous electrolyte solution further comprises a coating film forming agent.

17. The method for producing a nonaqueous electrolyte secondary battery according to claim 16, wherein the coating film forming agent comprises vinylene carbonate, monofluoroethylene carbonate, 1,3-propane sultone, or combinations of these.

18. The method for producing a nonaqueous electrolyte secondary battery according to claim 12, wherein the fluorinated solvent comprises at least one fluorinated linear carbonate and at least one fluorinated cyclic carbonate.

19. The method for producing a nonaqueous electrolyte secondary battery according to claim 12, wherein the nonaqueous electrolyte solution comprises a concentration of Additive A of from 0.001 mol/L to 3 mol/L.

20. The method for producing a nonaqueous electrolyte secondary battery according to claim 12, wherein the initial charging treatment is conducted at a voltage of from 4 V to 5 V and a charging rate of from 0.1 C to 0.2 C.

* * * * *